US00PP31690P3

(12) United States Plant Patent
Clark

(10) Patent No.: US PP31,690 P3
(45) Date of Patent: Apr. 21, 2020

(54) BLACKBERRY PLANT NAMED 'APF-205T'

(50) Latin Name: ***Rubus* subgenus *Rubus* Watson**
Varietal Denomination: APF-205T

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 15/999,920

(22) Filed: Aug. 30, 2018

(65) Prior Publication Data

US 2020/0077559 P1 Mar. 5, 2020

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./156, 203
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP15,788 | P2 | 6/2005 | Clark |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark et al. |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz et al. |
| PP26,405 | P3 | 2/2016 | Clark et al. |
| PP26,413 | P3 | 2/2016 | Ortiz et al. |
| PP26,990 | P3 | 8/2016 | Clark |
| PP27,032 | P2 | 8/2016 | Clark et al. |
| PP27,401 | P3 | 11/2016 | Clark et al. |
| PP28,598 | P3 | 11/2017 | Clark |

OTHER PUBLICATIONS

2012 Fruit and Vegetable Crops Research Report. eds: T. Coolong, J. Snyder and C. Smigell. file:///C:/Users/kredden/Desktop/2012%20fruit%20and%20vegetable%20crops%20research%20report.pdf. 3 pages. (Year: 2012).*

Fruit and Vegetable 2014 Research report. eds: S. Saha, J. Snyder and C. Smigell. http://www2.ca.uky.edu/agcomm/pubs/PR/PR688/PR688.pdf. 4 pages. (Year: 2014).*

* cited by examiner

*Primary Examiner* — Susan McCormick Ewoldt
*Assistant Examiner* — Karen M Redden
(74) *Attorney, Agent, or Firm* — Quarles & Brady LLP

(57) ABSTRACT

Description and specifications of a new and distinct blackberry cultivar named 'APF-205T' which originated from seed produced by a hand-pollinated cross of Arkansas selections 'APF-77' (U.S. Plant Pat. No. 24,249) x 'APF-49T' (non-patented, unreleased genotype) is provided. This new blackberry cultivar can be distinguished by its large fruit with consistent size and sweet flavor, thornless canes with consistently good plant health, and primocane-fruiting habit.

5 Drawing Sheets

Latin name: *Rubus* subgenus *Rubus* Watson.
Varietal denomination: 'APF-205T'.

BACKGROUND

The new primocane-fruiting blackberry cultivar called 'APF-205T' is described herein. The new cultivar originated from a hand-pollinated cross of Arkansas selections 'APF-77' (U.S. Plant Pat. No. 24,249) x 'APF-49T' (non-patented, unreleased genotype) made in 2005. The seeds resulting from this controlled hybridization were germinated in a greenhouse in the spring of 2006 and planted in a field near Clarksville, Ark. (West-Central Arkansas). The seedlings fruited in the summer of 2008 and one seedling, designated 'APF-205T', was selected. It was selected for its large fruit with consistent size and sweet flavor, thornless canes with consistently good plant health, and primocane-fruiting habit.

SUMMARY OF THE INVENTION

The new and distinct cultivar of blackberry originated from a hand-pollinated cross of Arkansas selections 'APF-77' (U.S. Plant Pat. No. 24,249) x 'APF-49T' (non-patented, unreleased genotype) made in 2005 and located near Clarksville, Ark. (West-Central Arkansas). The botanical designation of the new cultivar of blackberry is *Rubus* L. subgenus *Rubus* Watson. The seeds resulting from this controlled hybridization were germinated in a greenhouse in the winter to early spring of 2006 and planted in a field near Clarksville, Ark. The seedlings fruited in the summer of 2008 on floricanes and one seedling, designated 'APF-205T', was selected for its large fruit with consistent size and sweet flavor, thornless canes with consistently good plant health, and primocane-fruiting habit.

During 2008, the original plant selection was propagated asexually from root cuttings at the above-noted location, and a test row of 30 plants was established.

The new cultivar has been asexually multiplied since 2008 by the use of root cuttings, by rooting adventitious shoots from root cuttings and tissue culture. It forms new shoots from adventitious buds on root cuttings readily. During all asexual multiplication, the characteristics of the original plant have been maintained and no aberrant phenotypes have appeared. The cultivar differs from most blackberry cultivars which are floricane fruiting.

BRIEF DESCRIPTION OF THE PHOTOGRAPHS

The accompanying photographs show typical specimens of the new variety in color as nearly true as it is reasonably possible to make in a color illustration of this character. The plants shown in the figures are all three years of age.

DETAILED DESCRIPTION OF THE NEW CULTIVAR 'APF-205T'

Figure 1:
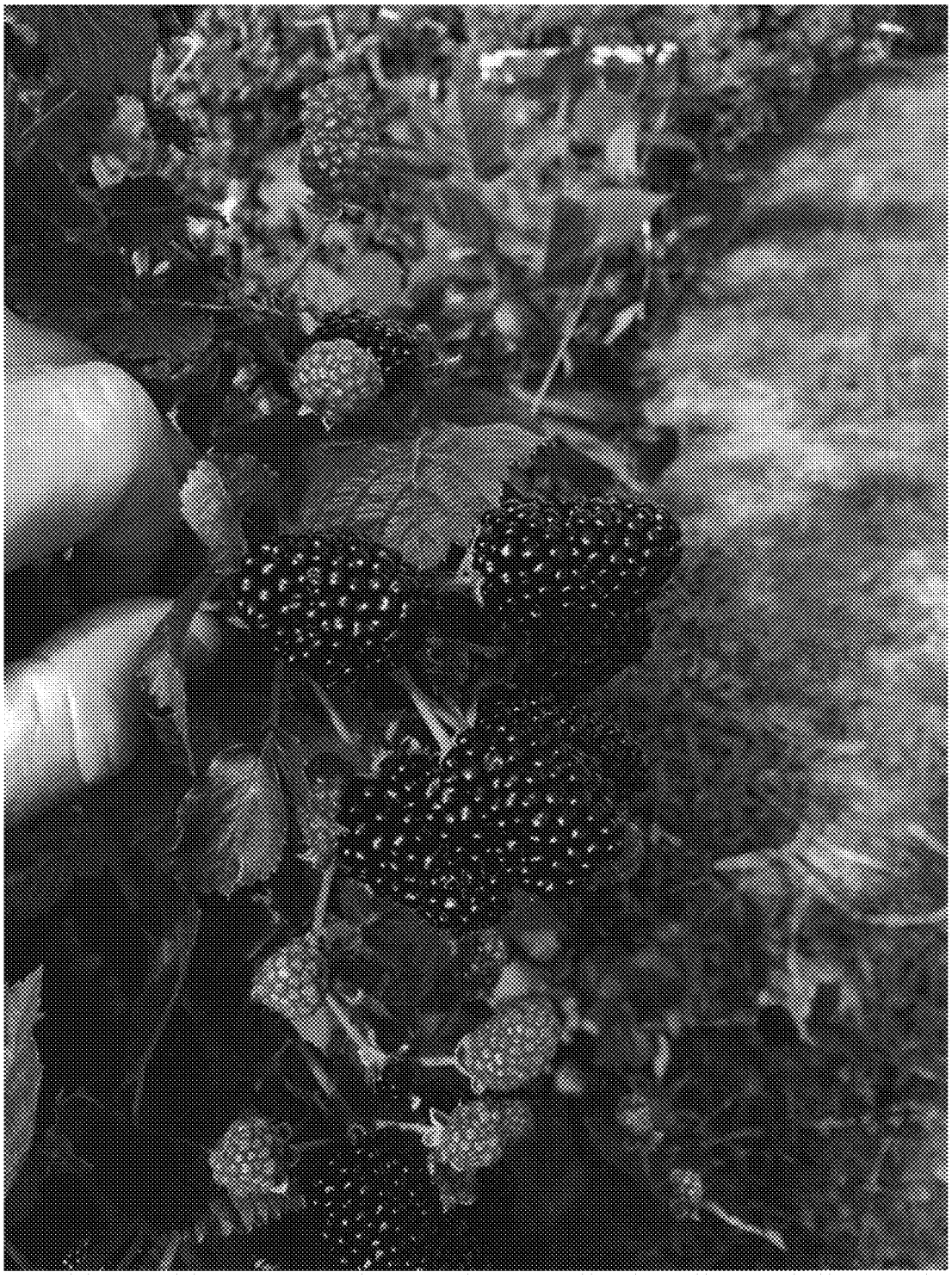
FIG. 1 is a photograph of fruits of 'APF-205T' borne on a floricane in mid-June, near Clarksville, Ark.
Figure 2:
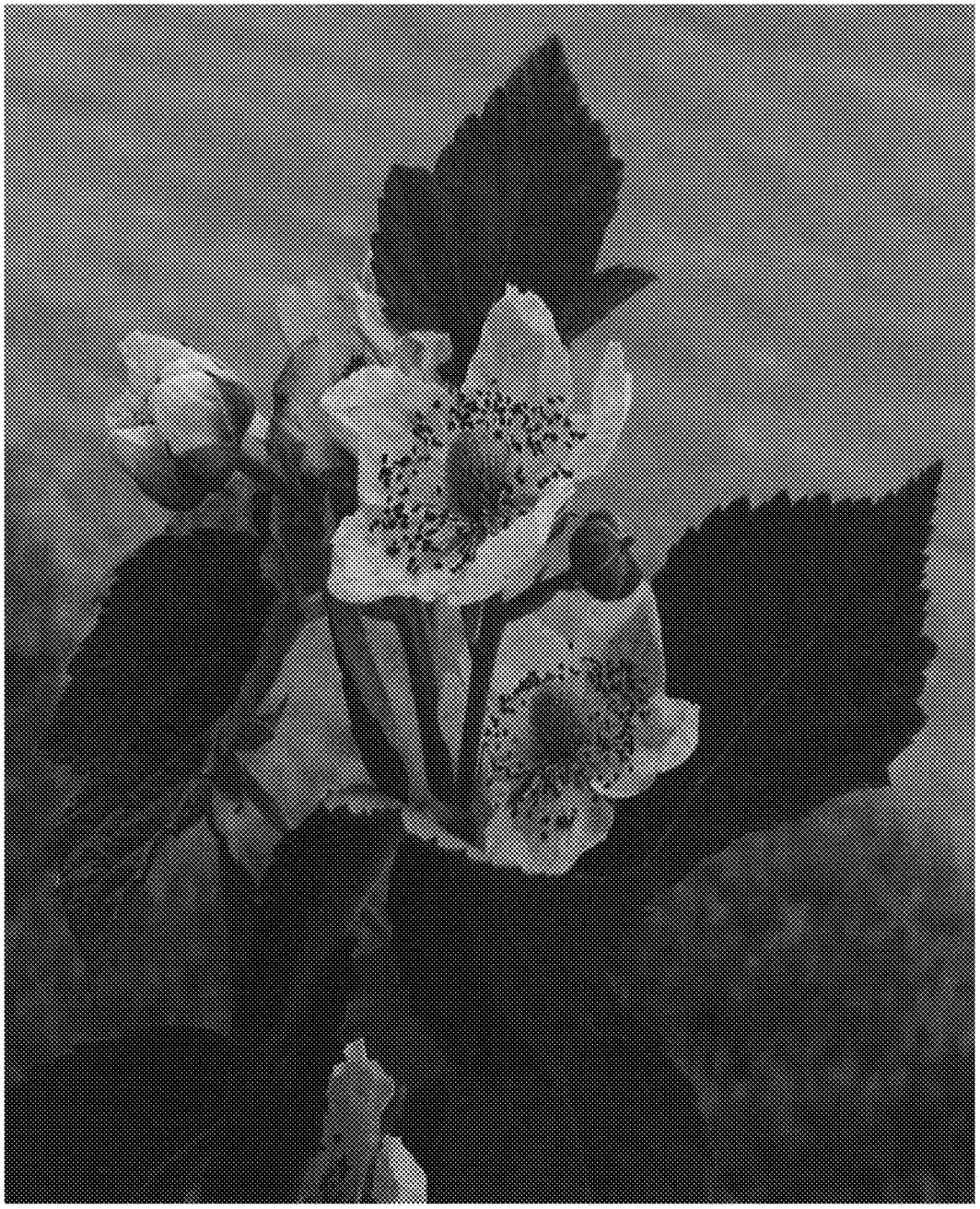
FIG. 2 is a photograph of primocane flowers and flower buds, near Clarksville, Ark. of 'APF-205T'.
Figure 3:
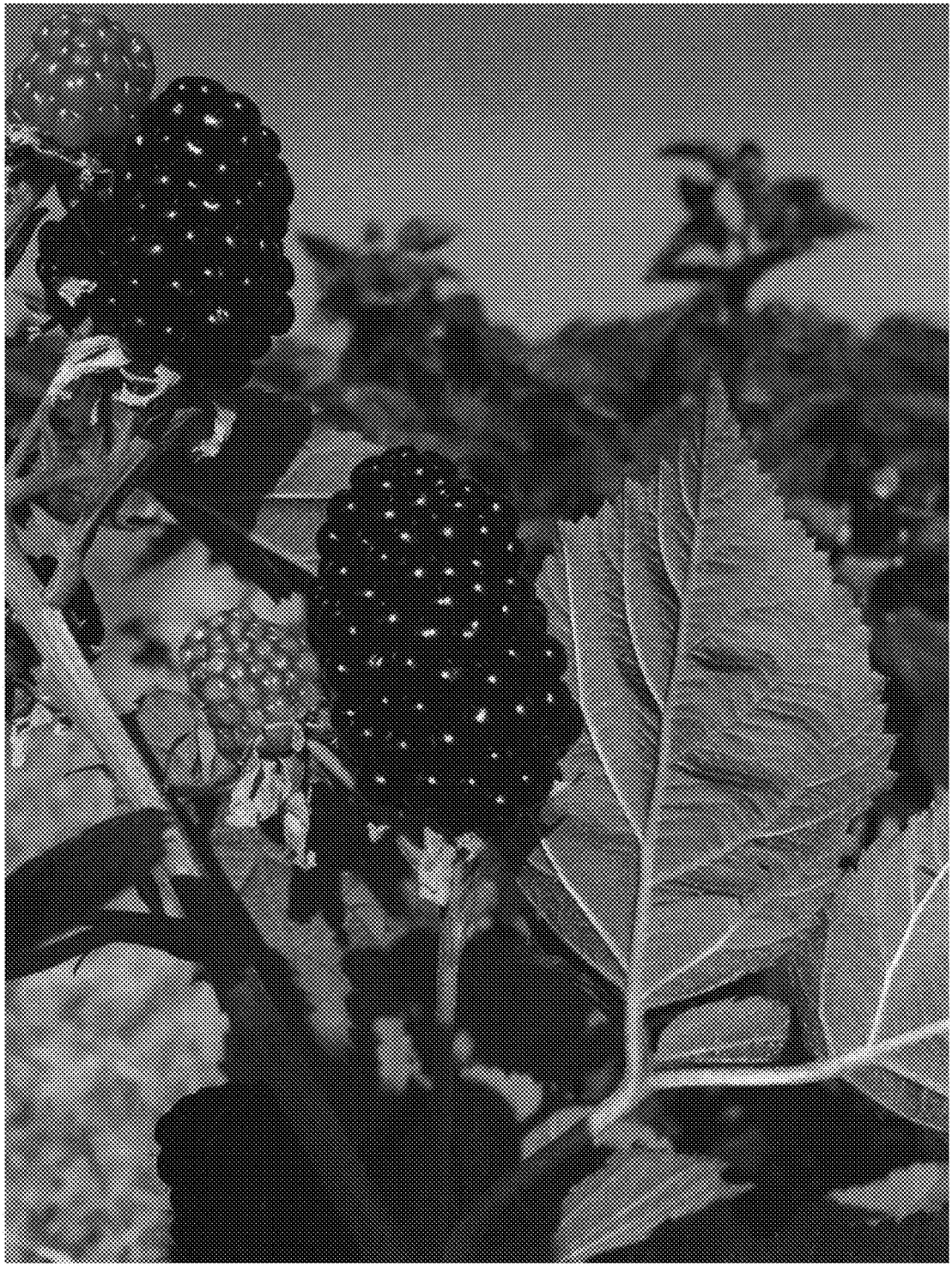
FIG. 3 is a photograph of fruit of 'APF-205T' produced on a primocane in late July, near Clarksville, Ark.
Figure 4:
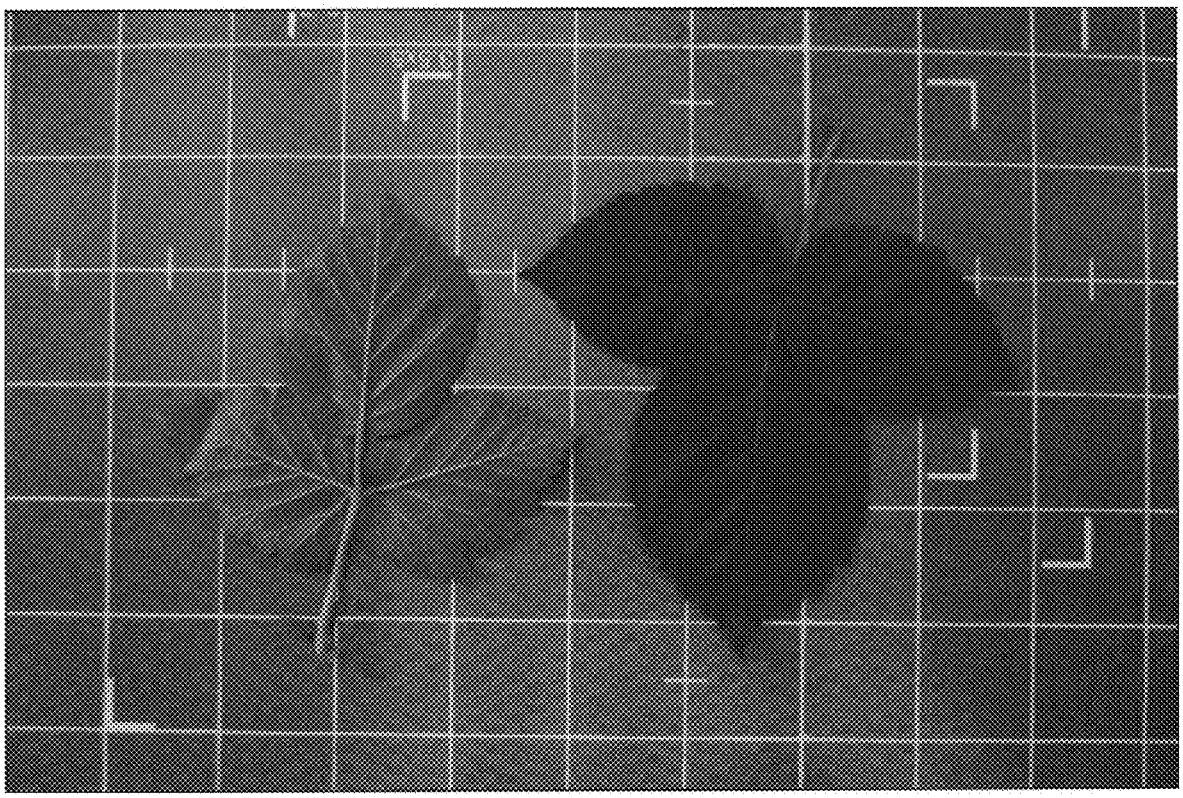
FIG. 4 is a photograph showing the abaxial (lower) and adaxial (upper) sides of floricane leaves, near Clarksville, Ark. of 'APF-205T'.
Figure 5:
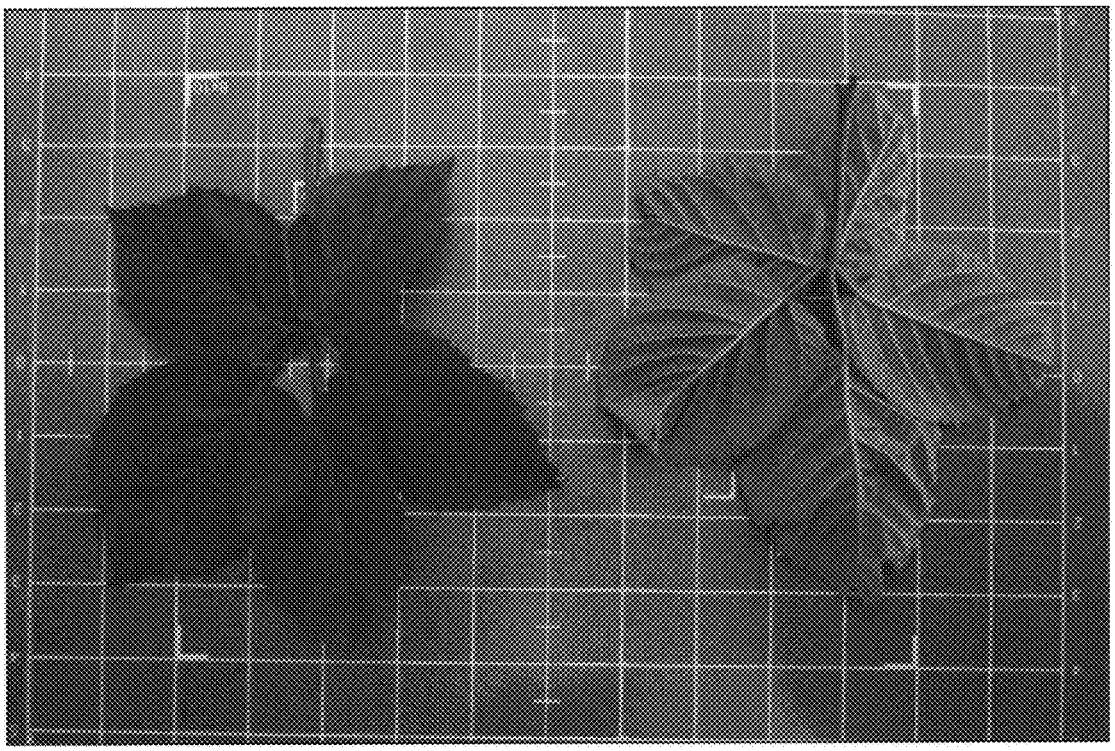
FIG. 5 is a photograph showing the abaxial (lower) and adaxial (upper) sides of primocane leaves, near Clarksville, Ark. of 'APF-205T'.

Plants and fruit of this new cultivar differ phenotypically from its parents. The new cultivar has larger fruit and thornless canes compared to its female parent 'APF-77'. The new cultivar is more productive and has larger fruit than male parent 'APF-49T'. Although blackberries (*Rubus* L. subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes are best managed if trained to a hedgerow and a trellis with supporting wires used to prevent canes from falling over due to wind or heavy fruit loads. The plants are thornless. Plants and fruit are moderately resistant to anthracnose (*Elsinoe veneta* (Burkh.) Jenkins), and plants have shown no evidence of susceptibility to orange rust (*Gymnoconia nitens* (Schwein.) F. Kern and H. W. Thurston). No screening has been done for resistance to double blossom/rosette (*Cercosporella rubi* (Wint.) Plakidas).

The floricane bloom period of the new cultivar begins on 16 April, compared to 1 April for 'APF-77'. Primocane bloom period begins 18 June compared to 10 June for 'APF-77'. Floricane fruit of the new cultivar has a harvest period of 36 days. Primocane first ripe fruit date was 18 July on tipped primocanes and whereas 'APF-77' is 15 July. Primocane fruit harvest can be dependent on environmental conditions, most importantly temperatures being below 32° C. (90° F.) to allow fruiting.

Fruit yields of the new cultivar on floricanes are usually 5.4 kg/plant (12.1 lb/plant) if the floricanes are retained for fruiting, compared to 3.5 kg/plant (7.7 lb) for 'APF-77' in West-Central Arkansas. Fruit yields of the cultivar on primocanes in West-Central Arkansas average 0.8 kg/plant (1.8 lb/plant) compared to 0.6 kg (1.3 lb/plant) for 'APF-77'.

The fruit shape is ovate, bright glossy black in color, and very attractive. The floricane fruit is large (7.1 g) while 'APF-77' averaged 6.5 g. Primocane fruit in West-Central Arkansas of the new cultivar averaged 9.2 g/berry. The berries have a very soft inner core or torus/receptacle, which provides for a very melting texture. The dry seed weight of floricane fruit for the new cultivar averaged 2.9 mg/seed, smaller than for 'APF-45' (U.S. Plant Pat. No. 22,449) (4.5 mg), 'Natchez' (U.S. Plant Pat. No. 20,891) (4.2 mg), and 'Ouachita' (U.S. Plant Pat. No. 17,162) (4.5 mg).

The fresh fruit rates very good in flavor, comparable to comparison cultivars. The soluble solids concentration averages 11.4% on shiny black fruit harvested from floricanes and is the same for primocane fruit (11.4%).

Primocane fruit and flowers are borne on the cane terminus or on lateral branches if primocanes are tipped, and fruiting continues down the primocane during the season. Canes usually attain a length of 1.5 to 1.8 m (4-5 ft) prior to the appearance of flower buds. The number of nodes down the cane that develop flowers is largely dependent on the length and conditions of the late summer to fall growing period.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation near Clarksville, Ark. The plants were fertilized near budbreak (late March on average) with complete or nitrogen fertilizer, and had an additional nitrogen fertilizer application in early July. Primocanes were tipped at approximately 1.14 m (45 inches), and grown in a hedgerow training system. Weeds were controlled with pre- and post-emergence herbicides supplemented with mechanical weed control activities. A single application of liquid lime sulfur was applied to the plants at budbreak, but no other fungicides were used. The descriptions reported herein are from specimens grown near Clarksville, Ark.

Plant:

*Size*.—Medium. Plants are grown in a hedgerow and primocanes tipped at approx. 114 cm; plants in this system range in size from approx. 135-140 cm tall and 91-102 cm wide.

*Growth habit*.—Moderate vigor, canes erect; suckers primarily from the crown.

*Growth rate*.—First emergence of primocanes is 19 April and primocanes reach tipping height (114 cm) approximately 16 June.

Productivity:

*Floricane*.—5.4 kg/plant (12.1 lb).

*Primocane*.—0.8 kg/plant (1.8 lb).

*Cold hardiness*.—Hardy to −13-−15° C. (4-8° F.) and possibly lower.

*Canes*.—Thornless, erect.

Floricane (dormant or winter cane):

*Cane diameter*.—Base: 1.80 cm; midpoint: 0.68 cm; terminal: 0.34 cm.

*Internode length*.—Base: 3.58 cm; midpoint: 3.34 cm; terminal: 2.02 cm.

*Floricane color*.—Base: Green group (137D); midpoint: Green group (137D); terminus: Green group (137C).

Primocane (current-season cane):

*Cane diameter*.—Base: 1.82 cm; midpoint: 1.19 cm; terminal: 1.05 cm.

*Internode length*.—Base: 7.34 cm; midpoint: 4.20 cm; terminal: 3.06 cm.

*Primocane color*.—Base: Grayed-purple group (187A); midpoint: Yellow-green group (144A); terminus: Grayed-purple group (183A). Anthocyanin coloration present on floricanes and primocanes.

*Date of primocane emergence*.—19 April.

*Lateral branching after tipping* (*measured at the end of growing season*).—Average number of lateral branches: 9.6; distribution full length of cane.

*Disease resistance*.—Moderate resistance to anthracnose, and no evidence of orange rust disease. No screening has been done for resistance to double blossom/rosette.

Foliage: Average date of Leaf bud burst: February 11.

Floricane:

*Leaves*.—Small; mature compound leaf width 8.69 cm; length 8.99 cm.

*Leaf shape*.—Compound leaf shape palmate.

*Glossiness*.—Abaxial: dull, pubescence lightly present; adaxial: dull, pubescence lightly present.

*Leaflet*.—Width: 3.86 cm; length: 5.52 cm; shape: ovate with acute apex and rounded subcordate base; margin: serrated; serration teeth length: 0.28 cm and width at base: 0.28 cm; pubescence: very light on both sides of leaflet; pubescence on abaxial and adaxial surfaces; number of leaflets per compound leaf: 3.

*Color*.—Base: abaxial: Green group (137C), adaxial: Green group (137A); midpoint: abaxial: Green group (137C), adaxial: Green group (137A); terminal: abaxial: Green group (137C), adaxial: Green group (137A).

*Petioles*.—Length: 2.81 cm; color: Yellow-green group (146C); texture: moderate pubescence.

*Petiolules*.—Length: 0.93 cm; Color: Yellow-green group (146C); texture: smooth, light pubescence.

*Stipules*.—Length: 1.19 cm; width: 0.22 cm.

*Shape*.—Overall: lanceolate; apex: acute; margin: entire (smooth); base: truncate.

*Texture*.—Abaxial: light to moderate pubescence; adaxial: light to moderate pubescence.

*Color*.—Abaxial: Yellow-green group (146D); adaxial: Yellow-green group (146D).

Primocane:

*Leaves*.—Medium; mature compound leaf: width: 16.64 cm; length 17.70 cm.

*Leaf shape*.—Compound leaf shape palmate.

*Glossiness*.—Abaxial: low to dull; adaxial: moderate pubescence.

*Leaflet*.—Width: 7.93 cm; length: 9.41 cm; shape: ovate with acute apex and cordate base; margin: serrated; serration tooth length: 0.19 cm; width at base: 0.25 cm; pubescence: very light on abaxial surface, heavy on adaxial surface; number of leaflets per compound leaf: 5.

*Color*.—Base: abaxial: Green group (137C); adaxial Green group (137A); midpoint: abaxial: Green group (137C); adaxial: Green group (137A); terminal: abaxial: Green group (137C); adaxial: Green group (137A).

*Petioles*.—Length: 7.16 cm; color: Yellow-green group (146B); texture: moderate to heavy pubescence.

*Petiolules*.—Length: 3.50 cm; color: abaxial: Purple group (183B); adaxial: Green group (148A); texture: light pubescence.

*Stipules*.—Length 1.48 cm; width: 0.19 cm.

*Shape*.—Overall: lanceolate; apex: acuminate; margin: entire; base: truncate.

*Texture*.—Abaxial: light to moderate pubescence; adaxial: light to moderate pubescence.

*Color*.—Abaxial: Purple group (185B), Green group (147C); adaxial: Purple group (185B), Green group (147C).

Flowers:

Floricane:

*Date of first bloom*.—6 April.

*Petal color*.—Abaxial: White group (155D); adaxial: White group (155D).

Reproductive organs:

*Stamens*.—Numerous.

*Pistils*.—Numerous.

*Pollen*.—Normal, fertile, and abundant.

*Flower diameter*.—3.36 cm.

*Flower depth*.—1.97 cm.

*Petal size*.—Length 1.94 cm; width 1.98 cm.

*Petal shape*.—Overall: ovate; apex: rounded; margin: sinuate; base: acuminate.

*Petal texture*.—Abaxial: no pubescence; adaxial; no pubescence.

*Average number flowers per cluster*.—7.4.

*Average number of petals per flower*.—5.2.

*Sepals*.—Length 0.61 cm; width: 0.50 cm.

*Sepals shape*.—Overall: lanceolate; apex: acute; margin: entire; base: truncate.

*Sepals texture*.—Abaxial: moderate-heavy pubescence; adaxial: heavy pubescence.

*Sepals color*.—Abaxial: Green group (138B); adaxial: Green group (138A).

*Number of sepals per flower*.—5.2.

*Pedicle*.—Length: 17.5 mm; color: Yellow-green group (146C); texture: light pubescence.

*Peduncle size*.—Length: 3.53 cm; width: 0.14 cm.

*Peduncle color*.—Green group (137B).

*Cyme type*.—simple cyme; length: 53.3 mm.

Primocane:

*Date of bloom*.—First bloom 18 June, and can extend until frost depending on environment and cultural management.

*Petal color*.—Abaxial: White group (155D); adaxial: White group (155D).

Reproductive organs:

*Stamens*.—Numerous.

*Pistils*.—Numerous.

*Pollen*.—Fertile and abundant unless temperatures exceed 32° C. (90° F.) at which temperature can damage flowers and anthers and pollen production can be reduced.

*Flower diameter.*—3.46 cm.
*Petal size.*—Length: 1.69 cm; width: 1.41 cm.
*Petal shape.*—Overall: obovate; apex: rounded; margin: sinuate; base: acuminate.
*Petal texture.*—Abaxial: no pubescence; adaxial: no pubescence.
*Average number flowers per cluster.*—11.
*Average number of petals per flower.*—5.
*Sepals.*—Length: 0.79 cm; width: 0.57 cm.
*Sepals shape.*—Overall: lanceolate; apex: aristate; margin: entire; base: truncate.
*Sepals texture.*—Abaxial: light pubescence; adaxial: light pubescence.
*Sepals color.*—Abaxial: Yellow-green group (144A); adaxial: Green group (143C).
*Number of sepals per flower.*—5.
*Pedicle length.*—2.67 cm; color: Yellow-green group (146C); texture: light pubescence.
*Peduncle size.*—Length: 2.37 cm; width: 0.13 cm.
*Peduncle color.*—Yellow-green group (146B).
*Cyme type.*—Elongated simple cyme; length: 17.25 cm.

Fruit:

Floricane:

*Maturity.*—Average first ripe date 3 June.
*Size.*—Large, 7.1 g average.
*Diameter of fruit at primary position on inflorescence.*—Equator: 2.28 cm; base pole: 1.71 cm; terminal pole: 1.30 cm.
*Diameter of fruit at secondary positions on inflorescence.*—Equator: 2.06 cm; base pole: 1.65 cm; terminal pole: 1.20 cm.
*Length (primary fruit).*—2.59 cm.
*Length (secondary fruit).*—2.11 cm.
*Length (tertiary fruit).*—2.23 cm.
*Shape.*—Ovate.
*Color.*—Black group (202A).
*Drupelet size.*—0.42 cm.
*Drupelets per berry.*—76.6.
*Seed size.*—Length: 2.66 mm; width: 1.63 mm.
*Seed weight.*—Wet: 3.2 mg; dry: 2.9 mg.
*Seed color.*—Wet: Grayed-red group (181A); dry: Grayed-orange group (165B).
*Soluble solids.*—11.4%.
*Ph.*—3.3.
*Acidity.*—0.8% citric acid.
*Processed quality.*—Not evaluated for processing.
*Uses.*—For home garden or local fresh-market use not requiring storage.

Primocane:

*Maturity.*—First ripe fruit date 18 July on tipped primocanes and can fruit until frost depending on environment and cultural management.
*Size.*—Large, 9.2 g/berry.
*Diameter of fruit at primary position on inflorescence.*—Equator: 2.33 cm; base pole: 2.24 cm; terminal pole: 1.40 cm.
*Diameter of fruit at secondary positions on inflorescence.*—Equator: 2.06 cm; base pole: 2.20 cm; terminal pole: 1.29 cm.
*Length (primary fruit).*—3.36 cm.
*Length (secondary fruit).*—3.10 cm.
*Length (tertiary fruit).*—2.93 cm.
*Shape.*—Ovate.
*Color.*—Black group (202A).
*Drupelet size.*—0.43 cm.
*Drupelets per berry.*—102.
*Seed size.*—Length: 2.94 mm; width: 1.69 mm.
*Seed weight.*—Wet: 6.8 mg; dry: 2.7 mg.
*Seed color.*—Wet: Grayed-red group (182A); dry: Grayed-orange group (165C).
*Soluble solids.*—11.4%.
*Ph.*—3.6.
*Acidity.*—0.36-1.25% citric acid.
*Processed quality.*—Not evaluated for processing.
*Uses.*—For home garden or local fresh-market use not requiring storage.

The cultivar: The most distinctive features of the new cultivar are large fruit with consistent size and sweet flavor, thornless canes with consistently good plant health, and primocane-fruiting habit.

I claim:

1. A new and distinct cultivar of blackberry plant named 'APF-205T', substantially as illustrated and described.

* * * * *